US012753141B2

(12) United States Patent
Jesus De Sequeira Serra Nunes et al.

(10) Patent No.: US 12,753,141 B2
(45) Date of Patent: Oct. 6, 2026

(54) CATALYTIC AND CONTINUOUS THERMOCHEMICAL PROCESS OF PRODUCTION OF VALUABLE DERIVATIVES FROM ORGANIC MATERIALS AND/OR WASTE

(71) Applicants: SECIL—COMPANHIA GERAL DE CAL E CIMENTO, S.A., Setúbal (PT); INSTITUTO SUPERIOR TÉCNICO, Lisbon (PT)

(72) Inventors: Angela Maria Jesus De Sequeira Serra Nunes, Azetiao (PT); João Carlos Moura Bordado, Lisbon (PT); Maria Joana Castelo De Assis Teixeira Neiva Correia, Cascais (PT); Maria Margarida Pires Dos Santos Mateus, Amadora (PT); Flávio Miguel Rocha Oliveira, Sintra (PT); Rui Miguel Galhano Dos Santos Lopes, Parede (PT)

(73) Assignees: SECIL—COMPANHIA GERAL DE CAL E CIMENTO, S.A., Setubal (PT); INSTITUTO SUPERIOR TECNICO, Lisbon (PT)

( * ) Notice: Subject to any disclaimer, the term of this patent is extended or adjusted under 35 U.S.C. 154(b) by 812 days.

(21) Appl. No.: 17/928,971

(22) PCT Filed: Jun. 2, 2020

(86) PCT No.: PCT/IB2020/055199
§ 371 (c)(1),
(2) Date: Dec. 1, 2022

(87) PCT Pub. No.: WO2021/245440
PCT Pub. Date: Dec. 9, 2021

(65) Prior Publication Data

US 2023/0132585 A1 May 4, 2023

(51) Int. Cl.
*C07C 51/48* (2006.01)
*C07C 37/72* (2006.01)
(Continued)

(52) U.S. Cl.
CPC .............. *C07C 51/48* (2013.01); *C07C 37/72* (2013.01); *C07C 59/185* (2013.01); *C07D 307/50* (2013.01); *C07H 1/08* (2013.01)

(58) Field of Classification Search
CPC ....... C07C 51/48; C07C 37/72; C07C 59/185; C07C 59/08; C07C 59/76; C10G 1/04; C07H 1/08
See application file for complete search history.

(56) References Cited

U.S. PATENT DOCUMENTS 5,730,837 A * 3/1998 Black ................. D21C 11/0007 162/77

FOREIGN PATENT DOCUMENTS

EP 2489780 * 8/2012 ............... D21C 3/20
EP 2489780 A1 * 8/2012 ............... D21C 3/20
(Continued)

*Primary Examiner* — Yate' K Cutliff
(74) *Attorney, Agent, or Firm* — Rivka Friedman

(57) ABSTRACT

The present invention relates to a novel liquid-liquid extraction process of a bio-oil obtained by an improved thermochemical process. This extraction process gives rise to two distinct phases: an organic phase, with bio-oil of energetic added value, and an aqueous phase, where the following can be obtained by chemical compounds with added value: lactic acid, formic acid, hydroxymethylfurfural, furfural, levulinic acid, monosaccharides, disaccharides and compounds with antioxidant properties, among others.

15 Claims, 1 Drawing Sheet

(51) Int. Cl.

| | |
|---|---|
| ***C07C 59/185*** | (2006.01) |
| ***C07D 307/50*** | (2006.01) |
| ***C07H 1/08*** | (2006.01) |

(56) References Cited

FOREIGN PATENT DOCUMENTS

| | | | | | |
|---|---|---|---|---|---|
| GB | 926034 | A | * | 5/1963 | ............. G05D 23/24 |
| WO | 2018085176 | A1 | | 5/2018 | |

* cited by examiner

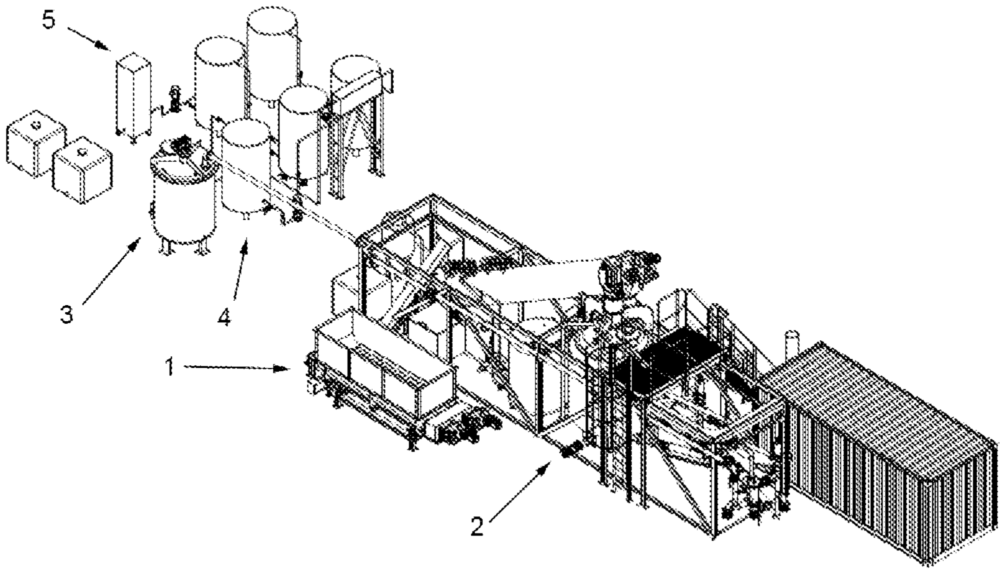
5
3
4
1
2

CATALYTIC AND CONTINUOUS THERMOCHEMICAL PROCESS OF PRODUCTION OF VALUABLE DERIVATIVES FROM ORGANIC MATERIALS AND/OR WASTE

FIELD OF THE INVENTION

The present invention falls within the scope of recycling with extraction of valuable derivatives, specifically recycling of waste from various industries, namely forest residues, vegetable residues, sludge from urban water treatment plants, livestock industry, paper, beer dreche, algae, food industry waste, including potato or tomato industry waste, pellets and pellet industry waste, fuel derived from waste and pellets of fuel derived from waste.

BACKGROUND OF THE INVENTION

The current market is open to the introduction of products of renewable sources, such as biofuels and added value biochemical products.

The search for innovative alternatives to waste reuse has in the recent past increased the exploration of alternatives via chemical extraction and/or reaction conversion of potential compounds existing on these sources.

However, the difficulty of implementing most of these processes on a larger scale lies in the production costs of the current processes.

The aim of the present invention is to introduce a new process of liquid-liquid extraction of added value products from a bio-oil (liquid fuel) by means of continuous thermochemical conversion of organic materials and/or waste.

The thermochemical conversion process of the present invention begins with the acid depolymerization and solvolysis of organic materials and/or waste, where the main components are cellulose, hemicellulose and lignin, proteins and other polymers and extractables. These components are depolymerized in the presence of a solvent giving rise to molecules of different molecular weights. These in turn lead to molecular rearrangements through the breakdown of ether linkages and decarboxylation reactions. These chemical reactions lead to the formation of added value compounds, including lactic acid, formic acid, hydroxymethylfurfural, furfural, levulinic acid, monosaccharides, disaccharides and compounds with antioxidant properties, among others.

The applicants of the present patent application are also applicants of the Portuguese patent application No. 108816 which discloses a batch or semi-batch process. The process referred to in the said application does not disclose a continuous process for the production of valuable derivatives from organic materials and/or waste, nor does it disclose the total recovery of the solvent used and the use of industrial waste from recycling and regeneration processes of mineral and vegetable oils used in other types of processes, as well as in washing waters with high content of these same residues.

In fact, said Portuguese patent application No. 108816 discloses the obtainment of a product (liquid fuel) which has a high content of sugars in its composition. The sugars are oxidizable compounds which reduce the calorific value of the mixture. The present patent application allows the sugars to be separated, thus causing a liquid fuel to be obtained with a much higher calorific value. The sugars separated by the process of the present invention are used as raw material for the production of bioethanol, bioplastics, feeds, food applications, biosurfactants and biolubricants, thus providing for the deepening of the circular economy.

In effect the process of the present invention discloses a phase extraction process which includes added value compounds such as sugars and molecular rearrangements thereof from the cellulosic matrix, polyols and aromatics originated from the lignin fraction. In the case of organic waste, in addition to the above-mentioned components, it may contain proteins and fats. The proteins have in their composition high levels of nitrogen, which can lead to the poisoning of the catalysts in most of the thermochemical conversion processes. In the case of the process of the present invention, this problem is circumvented by the use of alcohols such as 1-octanol, or 2-octanol or 2-ethylhexanol, glycols, glycerine or mixtures thereof with used mineral and vegetable oils from recycling processes and regeneration of industrial processes. The use of these solvents improves the homogenization of the reaction medium leading to lower viscosity contents and allowing an increase in process conversion, thus enabling to obtain value added products with nitrogen. These compounds will be dissolved and extracted in the aqueous phase during the extraction process and may later be used in some applications, namely in soil improvement.

As regards the search for innovative alternatives for the reuse of waste so that added-value products are obtained, there has been some work.

In patent application WO 2014087015, the method employed to obtain levulinic acid and formic acid distinguishes from the process of the present invention in that it comprises a solid-liquid extraction followed by extractions by organic solvents from slurry obtained by the hydrolysis of the cellulosic part only of biomass.

The patent U.S. Pat. No. 9,073,841 discloses a method for the preparation of levulinic acid, which is very similar to that of the patent mentioned in the previous paragraph, using a higher concentration of acid in the hydrolysis step and again using a liquid-solid extraction with organic solvents.

The closest documents to the present application disclose the use of organic solvents for the extraction of added-value compounds. They do not, however, mention the possibility of using water as the solvent, as in the present invention, more specifically water from the distillation of moisture from organic materials and/or waste and reaction water, which makes the process of the patent application a very much affordable and sustainable one. These facts are disclosed in order to illustrate the technical problem addressed by the present disclosure.

SUMMARY OF THE INVENTION

The present invention discloses an acid depolymerization and solvolysis process of organic materials and/or waste, wherein the main components are cellulose, hemicellulose and lignin, proteins and other polymers and extractables. These components are depolymerized in the presence of a solvent giving origin to molecules of different molecular weights. These in turn lead to molecular rearrangements through decarboxylation reactions and breakage of ether and ester linkages. These chemical reactions lead to the formation of compounds with added value, including lactic acid, formic acid, hydroxymethylfurfural, furfural, levulinic acid, monosaccharides, disaccharides and compounds with antioxidant properties, among others.

In a preferred embodiment the present invention discloses a process for the production of derivatives from organic materials and/or waste, characterized in that it comprises the following steps:

a) continuous depolymerization and solvolysis of organic materials and/or waste which are added continuously;
b) liquid-liquid extraction of sugars, polysaccharides and phenolic compounds of the product obtained in (a) by adding a mass amount of from 10 to 75% water, preferably distilled water or condensed water, ethanol or a mixture of water and ethanol, thus obtaining an organic phase and an aqueous phase;
c) distillation of the organic phase of the product obtained in b);
d) evaporation of the volatile compounds of the product obtained in b).

In a further embodiment, the invention relates to a process wherein said organic materials and/or waste are added at a rate of 10 to 50%/hour (w/w) relative to the mass of the solvent or mixture of solvents in the presence of a component selected from the following list: organic or mineral acid catalyst, glycol, glycerine, alcohol, mineral oil, vegetable oil, residues from the industrial processes of recycling and regeneration of waste oils and mixtures thereof.

In a further embodiment, the invention relates to a process wherein the boiling point of the phase obtained in step c) ranges from 100 to 240° C.

In a further embodiment, the invention relates to a process wherein the ratio between depolymerized product obtained in step a) and relative to the amount of organic materials and/or waste inserted, is between 70 and 99% (w/w).

In a further embodiment, the invention relates to a process, wherein said organic materials and/or waste are selected from the list: forest residues, vegetable residues, sludge from urban water treatment plants, livestock industry, sludge from the paper industry, beer dreche, algae, food industry waste including residues from the potato or tomato industry, pellets and pellet industry waste, fuel derived from waste and pellets of fuel derived from waste.

In a further embodiment, the invention relates to a process, wherein said glycol is selected from the list: DEG and glycerine; and the solvents are selected from the list: 1-octanol, 2-octanol, 2-ethylhexanol, mineral and vegetable oils, industrial waste from the regeneration and recycling processes of used mineral and vegetable oils.

In a further embodiment, the invention relates to a process, wherein said solvents or the solvent mixture is distilled with water, preferably in a range of 5 to 60% (w/w).

In a further embodiment, the invention relates to a process, wherein said organic materials and/or waste comprise water between 0.1 and 90% (w/w).

In a further embodiment, the invention relates to a process, wherein said organic materials and/or waste have in their composition, preferably, a water content between 30 and 60% (w/w).

In a further embodiment, the invention relates to a process, wherein said aqueous phase of step b) comprises recoverable compounds, said compounds being selected from the following list: levulinic acid, mono-, di- and trisaccharide sugars, furfural, 5-hydroxymethyl furfural and lactic acid, preferably at a concentration of between 3 and 99% (dry w/w).

In a further embodiment, the invention relates to a process, wherein said organic phase of step b) comprises an alcohol content between 1 and 50% and phenolic compounds (w/w).

In a further embodiment, the invention relates to a process, characterized in that the rate of product production and withdrawal is in the range of 5 to 100% (w/w) relative to the inserted waste.

In a further embodiment, the invention relates to a process, wherein said organic acid catalyst of step a) is added in an amount of 0.5 to 5% by mass relative to the total weight of the composition of the solvent reaction mixture and is selected from p-toluenesulfonic acid and sulfuric acid.

In a further embodiment, the invention relates to a process, wherein said mineral acid catalyst of step a) is added in an amount of 0.5 to 5% ($w_{mineral\ acid\ catalyst}/w_{total\ weight\ of\ reaction\ mixture}$) and is selected from the following list: aluminium sulphate and aluminium chloride.

In a further embodiment, the invention relates to a process, wherein said liquid-liquid extraction of step b) is carried out with at least one solvent selected from the following list: water, distilled water, condensed water in step a), ethanol or a mixture of water and ethanol.

In a further embodiment, the invention relates to a process, wherein the temperature of said acid depolymerization is between 120° C. and 180° C.

In a particular embodiment, the invention refers to an installation for carrying out the process of the present invention, characterized in that it comprises:

an assembly (1) of collecting canvas, chain conveyor and worm;
a reactor (2);
a mixing tank (3);
an equipment for separation (4) of the oil-sugar solution mixture;
a distillation equipment assembly (5) comprising a distillation column under reduced pressure, in order to enable the distillation of the oil within the range of step c); and
a thin film distiller for obtaining sugars in step d).

BRIEF DESCRIPTION OF THE DRAWINGS

The following FIGURE provides preferred embodiments for illustrating the disclosure and should not be seen as limiting the scope of invention.

FIG. 1 represents the installation wherein the process of this invention is carried out.

DETAILED DESCRIPTION OF THE INVENTION

The process of the present invention relates to a continuous catalytic thermochemical process involving the production of valuable derivatives from organic materials and/or waste.

The process begins with acid depolymerization of the organic matter by continuous addition of the organic materials at a rate of 10-50% per hour by mass relative to the mass of solvent or mixture of solvents in the reactor.

Then an organic or mineral acid catalyst such as p-toluenesulfonic acid or aluminium sulphate, respectively, is added. This acid catalyst is initially added into the reactor in an amount within the range of 0.5%-5% by mass. The aluminium sulphate is inserted anhydrous or in aqueous solution with a concentration between 5-95% by mass. These catalysts show fast and efficient conversions, which are economically favourable to their application in a continuous process.

The organic materials which are susceptible of being used in the process of the present patent application are forest and vegetable waste, sludge from urban water treatment plant, livestock industry waste, sludge from the paper industry, beer dreche, algae, food industry waste, including residues from the potato or tomato industry, pellets and pellet industry residues, fuel derived from waste and pellets of fuel derived from waste. The material should have in its composition water contents between 0.1 and 90%, the range of 30-60% being considered optimum in terms of reaction.

The depolymerization occurs at atmospheric pressure and at temperatures between 120° C. and 180° C. This temperature is required to minimize the formation of humic compounds and coals due to secondary reactions at low temperatures.

The addition of organic materials and/or waste is carried out continuously at a rate of 10-50% per hour relative to the amount of the reaction bath existing in the reactor.

The rate of product production and withdrawal thereof in continuous process contemplates the moisture present in the initial waste. Therefore, a rate in the range of 5 to 100% by mass can be withdrawn relative to the inserted, considering a conversion within the range of 70-99% of organic materials and/or waste added on dry basis.

In the process of the present invention the solvent or mixture of solvents will be distilled from the reaction mixture together with the water present in the organic materials and/or waste inserted in a range of 5 to 60% of mass concentration. These solvents, in addition to improving the homogenization of the reaction medium, also allow recovery at a rate of 5-100% of the total solvent mixture added.

Throughout the process it is possible to also recover all the water originating from both the latent moisture in the materials and the reaction water.

To the product resulting from the catalytic thermochemical process should be added a mass amount of 10 to 75% of water, namely condensed water, ethanol or mixtures of water and ethanol, in the mixer tank for liquid-liquid extraction. If this step is not carried out, the product will be considered as crude liquid fuel.

With this reaction step, the process involves a subsequent recovery of the product resulting from the catalytic continuous thermochemical process through a simple liquid-liquid extraction with water. During the extraction two phases will be formed: an aqueous phase and an organic phase.

The aqueous phase may have varying amounts of valuable compounds, among which levulinic acid, mono-, di- and trisaccharide sugars, furfural, 5-hydroxymethyl furfural and lactic acid in mass quantities ranging from 3 to 99% on a dry basis.

In the organic phase there will be solvent contents between 1-50% and phenolic compounds with high antioxidant activity. After extraction of the aqueous phases, a thin film distillation will be carried out in order to remove both the solvents and the water without degrading the remaining constituents, enabling the recovery of the other fractions. The organic phase will undergo distillation under reduced pressure. The fractions corresponding to the lower phases of the ranges of temperature 100-150 and 200-215° C. have (estimated) higher calorific values, which are quite interesting and of the same order of magnitude of the natural gas. The distilled fraction in the range of temperature from 200 to 240° C. will correspond to a complex combination of (aliphatic, naphthenic and aromatic) hydrocarbons whose carbon number varies between C9 and C16. This fraction can be considered an alternative fuel, derived from biomass, i.e. biokerosene.

The object of the present invention is a catalytic and continuous thermochemical process for the production of valuable derivatives from organic materials and/or waste, comprising the following steps:

a) acid continuous depolymerization and solvolysis of organic materials and/or waste which are continuously added at a rate of 10 to 50%/hour by mass relative to the mass of the solvent or mixture of solvents and in the presence of an organic or mineral acid catalyst, glycols, glycerine, alcohols, mineral and vegetable oils, and residues from the industrial processes of recycling and regeneration of waste oils and mixtures thereof;

b) liquid-liquid extraction of sugars, polysaccharides and phenolic compounds of the product obtained in (a) by adding a mass amount of from 10 to 75% water, such as distilled water or condensed water, ethanol or a mixture of water and ethanol, thus obtaining an organic phase and an aqueous phase;

c) distillation of the oil phase of the product obtained in b) wherein the obtained phase has boiling points ranging from 100 to 240° C.;

d) evaporation of the volatile compounds of the product obtained in b), thus obtaining polysaccharide and simple sugars.

In a preferred embodiment, a depolymerized product is obtained in step a) at a conversion rate between 70 and 99% by mass relative to the amount of organic materials and/or waste inserted.

In an even more preferred embodiment, the organic materials and/or waste are selected from among forest residues, vegetable residues, sludge from urban water treatment plants, livestock industry, sludge from the paper industry, beer dreche, algae, food industry waste, including residues from the potato or tomato industry, pellets and pellet industry residues, fuel derived from waste and pellets of fuel derived from waste.

Preferably the solvents used in step a) are DEG-type glycols (diethyleneglycol) and glycerine, alcohols selected from 1-octanol, or 2-octanol or 2-ethyl-hexanol, mineral or vegetable oils and industrial waste from the recycling and regeneration of used mineral and vegetable oils.

Preferably, these solvents or solvent mixtures are distilled together with water in a range of from 5 to 60% by mass and reused.

In a preferred embodiment, the organic materials and/or waste to be depolymerized have in their composition water contents between 0.1 and 90%. Even more preferably, the organic materials and/or waste have in their composition water contents between 30 and 60%.

Preferably, the organic acid catalyst used in step a) is added in an amount of 0.5 to 5% by mass relative to the total weight of the composition and is selected from p-toluenesulfonic acid and sulfuric acid.

In another preferred mode, the mineral acid catalyst of step a) is added in an amount of 0.5 to 5% by mass relative to the total weight of the composition and is selected from aluminium sulphate and aluminium chloride.

Preferably, the acid depolymerization takes place at a temperature between 120° C. and 180° C.

Preferably, the organic phase of step b) has a content of solvent or solvent mixtures between 1 and 50% and phenolic compounds, by mass, in the remainder.

In a preferred embodiment the aqueous phase of step b) comprises valuable compounds, among which levulinic acid, mono-, di- and trisaccharide sugars, furfural, 5-hydroxymethyl furfural and lactic acid in mass quantities which may be between 3 and 99% on dry basis.

It is also an object of the present invention an apparatus for carrying out a catalytic and continuous thermochemical process for the production of valuable derivatives from organic materials and/or waste, which comprises:

an assembly (1) of collecting canvas, chain conveyor and worm for dosing the organic materials and/or waste added in the acid depolymerization process of step a);

a reactor (2) where the acid depolymerization of step a) occurs;

a mixing tank (3) for liquid-liquid extraction, where the step b) of claim 1 occurs;

equipment for separation (4) of the oil-sugar solution mixture, contemplated in step b);

an equipment assembly (5) for distilling the oil phase at various temperatures and pressures in order to obtain the various fractions of different calorific values and for the thin film distillation of the aqueous phase, so that the dissolved sugars turn into concentrated syrups for different applications, where step d) occurs.

It is yet another object of the invention to use the product obtained by the catalytic and continuous thermochemical process aimed at the production of valuable derivatives from organic materials and/or waste in the production of bioethanol, bioplastics, animal feeds, food and cosmetic applications, from the aqueous phase, and biosurfactants, biolubricants, biopolyols and biofuels, from the organic phase.

EXAMPLES

Example 1

Continuous addition, through the assembly (1), of 100 kg/hr of forest residues, such as eucalyptus sawdust, on 40% wet basis, in the reactor (2) containing 600 kg of 2-ethyl-hexanol and 6 kg of p-toluenesulfonic acid. From this value is withdrawn the same mass value as that which was added of forest residues on a dry basis, kg of product, containing a complex mixture of phenolic compounds, glycosides, levulinic acid, mono-, di- and trisaccharide sugars, furfural and 5-hydroxymethyl furfural, to be extracted in the next step. Forest residues, such as eucalyptus sawdust, will be continuously added to the reactor (2) at a rate of 100 kg/hr and the same mass value of forest residues (eucalyptus sawdust), on a dry basis, per hour of liquefied, is withdrawn. The temperature within the reactor (2) is in the range of 120° C. to 180° C.

The product obtained by this catalytic thermochemical process is subjected to a liquid-liquid extraction in the separation equipment (4) in the presence of condensed water obtained. The extraction is carried out in an amount of 50% of the product mass per 50% of condensed water. Two distinct fractions are obtained, an aqueous phase and an organic phase. The aqueous fraction is distilled by the equipment assembly (5) through the thin film evaporator and consists of recoverable products, such as levulinic acid, mono-, di- and trisaccharide sugars, furfural, 5-hydroxymethyl furfural and lactic acid.

The organic phase is concentrated by distillation in the equipment assembly (5) under reduced pressure.

For the characterization of this product, DPPH (2,2-diphenyl-1-picrylhydrazyl) was chosen, the latter being the most common, among the various existing methods to evaluate the antioxidant activity. This assay is referred to as IC50, i.e. the concentration required to reduce 50% of the DPPH radical, wherein the lower the IC50 value, the greater the antioxidant activity of the material. Therefore, in this case the value obtained for the product was within the range of 12 to 15 mg/ml.

Example 2

Continuous addition, through the assembly (1), of 200 kg/hr of pellets, on a 20% wet basis, to the reactor (2) containing 800 kg of 2-ethyl-hexanol and 24 kg of aluminium sulphate. From this value is withdrawn the same mass value as that which was added of pellet residues on a dry basis, per kg of product, containing a complex mixture of phenolic compounds, glycosides, levulinic acid, mono-, di- and trisaccharide sugars, furfural and 5-hydroxymethyl furfural, to be extracted in the next step. Pellet residues will be continuously added to the reactor (2) at a rate of 200 kg/hr and the same mass value is withdrawn from pellet residues on a dry basis per hour of liquefied. The temperature inside the reactor (2) is within the range of 120° C. to 180° C.

The product obtained by this catalytic thermochemical process is subjected to a liquid-liquid extraction in the separation equipment (4) in the presence of distilled water. The extraction is carried out in an amount of 50% of the product mass per 50% of distilled water. Two distinct fractions are obtained, an aqueous phase and an organic phase. The aqueous fraction is distilled by the equipment assembly (5) through the thin film evaporator and consists of recoverable products, such as levulinic acid, mono-, di- and trisaccharide sugars, furfural, 5-hydroxymethyl furfural and lactic acid.

The organic phase is concentrated by distillation in the equipment assembly (5) under reduced pressure.

For the characterization of this product, DPPH (2,2-diphenyl-1-picrylhydrazyl) was chosen, as the most common, among the various existing methods to evaluate the antioxidant activity. This assay is referred to as IC50, i.e. the concentration required to reduce 50% of the DPPH radical, wherein the lower the IC50 value, the greater the antioxidant activity of the material. Therefore, in this case the value obtained for the product was within the range of 3 to 5 mg/ml.

Example 3

Continuous addition, through the assembly (1), of 100 kg/hr of pellets, on a 15% wet basis, into the reactor (2) containing 850 kg of 2-ethyl-hexanol and 25.6 kg of aluminium sulphate. From this value is withdrawn the same mass value as that which was added of pellets, on dry basis, per kg of product, containing a complex mixture of phenolic compounds, glycosides, levulinic acid, mono-, di- and trisaccharide sugars, furfural and 5-hydroxymethyl furfural, to be extracted in the next step. Pellets will be continuously added to the reactor (2) at a rate of 100 kg/hr and the same mass value of pellets per hour of liquefied is withdrawn. The temperature inside the reactor (2) is within the range of 120° C. to 180° C.

The product obtained by this catalytic thermochemical process is subjected to a liquid-liquid extraction in the separation equipment (4) in the presence of 50%/50% water and ethanol solution. The extraction is carried out in an amount of 50% of the product mass per 50% of water and ethanol solution. Two distinct fractions are obtained, an aqueous phase and an organic phase. The aqueous fraction is distilled by the equipment assembly (5) through the thin film evaporator and consists of recoverable products, such as levulinic acid, mono-, di- and trisaccharide sugars, furfural, 5-hydroxymethyl furfural and lactic acid.

The organic phase is concentrated by distillation, in the distillation equipment assembly (5) under reduced pressure.

For the characterization of this product, DPPH (2,2-diphenyl-1-picrylhydrazyl) was chosen, the latter being the most common, among the various existing methods to evaluate the antioxidant activity. This assay is referred to as IC50, i.e. the concentration required to reduce 50% of the DPPH radical, wherein the lower the IC50 value, the greater the antioxidant activity of the material. Therefore, in this case the value obtained for the product was within the range of 3 to 5 mg/ml.

Example 4

Continuous addition, through the assembly (1), of 200 kg/hr of waste from the animal industry, e.g. pork slurries, on 60% wet basis, to the reactor (2) containing 400 kg of 2-octanol and 12 kg of p-toluenesulfonic acid. From this value is withdrawn the same mass value as that which was added of waste from the animal industry on dry basis, per kg of product, containing a complex mixture of phenolic compounds and glycosides, to be extracted in the next step. Waste from animal industry will be continuously added to the reactor (2) at a rate of 200 kg/hr and the same mass value of waste from animal industry, on dry basis, per hour of liquefied is withdrawn. The temperature inside the reactor (2) is within the range of 120° C. to 180° C.

The product obtained by this catalytic thermochemical process is subjected to a liquid-liquid extraction in the separation equipment (4) in the presence of condensed water obtained. The extraction is carried out in an amount of 50% of the product mass per 50% of condensed water. Two distinct fractions are obtained, an aqueous phase and an organic phase. The aqueous fraction is distilled by the equipment assembly (5) through the thin film evaporator and consists of recoverable products.

The organic phase is concentrated by distillation, in the equipment assembly (5) under reduced pressure. For the characterization of this product, DPPH (2,2-diphenyl-1-picrylhydrazyl) was chosen, the latter being the most common, among the various existing methods to evaluate the antioxidant activity. This assay is referred to as IC50, i.e. the concentration required to reduce 50% of the DPPH radical, wherein the lower the IC50 value, the greater the antioxidant activity of the material. Therefore, in this case the value obtained for the product was within the range of 20 to 30 mg/ml.

Example 5

Continuous addition, through the assembly (1), of 300 kg/hr of waste from the paper industry, as for instance its sludge, on 70% wet basis, to the reactor (2) containing 300 kg of 2-ethyl-hexanol and 9 kg of p-toluenesulfonic acid. From this value is withdrawn the same mass value as that which was added of waste from the paper industry on dry basis, per kg of product, containing a complex mixture of phenolic compounds, glycosides, levulinic acid, mono-, di- and trisaccharide sugars, furfural and 5-hydroxymethyl furfural, to be extracted in the next step. Waste from the paper industry will be continuously added to the reactor (2) at a rate of 300 kg/hr and the same mass value of waste from the paper industry, on dry basis, per hour of liquefied is withdrawn. The temperature inside the reactor (2) is within the range of 120° C. to 180° C.

The product obtained by this catalytic thermochemical process is subjected to a liquid-liquid extraction in the separation equipment (4) in the presence of condensed water obtained. The extraction is carried out in an amount of 50% of the product mass per 50% of condensed water. Two distinct fractions are obtained, an aqueous phase and an organic phase. The aqueous fraction is distilled by the equipment assembly (5) through the thin film evaporator and consists of recoverable products, such as levulinic acid, mono-, di- and trisaccharide sugars, furfural, 5-hydroxymethyl furfural and lactic acid.

The organic phase is concentrated by distillation, in the equipment assembly (5) under reduced pressure.

For the characterization of this product, DPPH (2,2-diphenyl-1-picrylhydrazyl) was chosen, the latter being the most common, among the various existing methods to evaluate the antioxidant activity. This assay is referred to as IC50, i.e. the concentration required to reduce 50% of the DPPH radical, wherein the lower the IC50 value, the greater the antioxidant activity of the material. Therefore, in this case the value obtained for the product was within the range of 20 to 30 mg/ml.

Example 6

Continuous addition, through the assembly (1), of 200 kg/hr of food waste, e.g. potato peelings, on 60% wet basis, to the reactor (2) containing 400 kg of 2-ethyl-hexanol and DEG and 12 kg of p-toluenesulfonic acid. From this value is withdrawn the same mass value as that which was added of waste from the food industry, on dry basis, per kg of product, containing a complex mixture of phenolic compounds, glycosides, levulinic acid, mono-, di- and trisaccharide sugars, furfural and 5-hydroxymethyl furfural, to be extracted in the next step. Food waste will be continuously added to the reactor (2) at a rate of 200 kg/hr and the same mass value of food waste, on dry basis, per hour of liquefied is withdrawn. The temperature inside the reactor (2) is within the range of 120° C. to 180° C.

The product obtained by this catalytic thermochemical process is subjected to a liquid-liquid extraction in the separation equipment (4) in the presence of water. The extraction is carried out in an amount of 50% of the product mass per 50% of water. Two distinct fractions are obtained, an aqueous phase and an organic phase. The aqueous fraction is distilled by thin film evaporation and consists of recoverable products, such as levulinic acid, mono-, di- and trisaccharide sugars, furfural, 5-hydroxymethyl furfural and lactic acid.

The organic phase is concentrated by distillation, in the distillation equipment assembly (5) under reduced pressure.

For the characterization of this product, DPPH (2,2-diphenyl-1-picrylhydrazyl) was chosen, the latter being the most common, among the various existing methods to evaluate the antioxidant activity. This assay is referred to as IC50, i.e. the concentration required to reduce 50% of the DPPH radical, wherein the lower the IC50 value, the greater the antioxidant activity of the material. Therefore, in this case the value obtained for the product was within the range of 20 to 25 mg/ml.

Example 7

Continuous addition, through the assembly (1), of 100 kg/hr of waste-derived fuel, on 30% wet basis, to the reactor (2) containing 700 kg of 2-ethyl-hexanol and mineral or vegetable oil and 21 kg of p-toluenesulfonic acid. From this value is withdrawn the same mass value as that which was added of waste-derived fuel, on dry basis, per kg of product, containing a complex mixture of phenolic compounds, glycosides, levulinic acid, mono-, di- and trisaccharide sugars, furfural and 5-hydroxymethyl furfural, to be extracted in the next step. Waste-derived fuel will be continuously added to the reactor (2) at a rate of 100 kg/hr and the same mass value of waste-derived fuel, on dry basis, per hour of liquefied, is withdrawn. The temperature inside the reactor (2) is within the range of 120° C. to 180° C.

The product obtained by this catalytic thermochemical process is subjected to a liquid-liquid extraction in the separation equipment (4) in the presence of 50%/50% water and ethanol solution. The extraction is carried out in an amount of 50% of the product mass per 50% of the solution mass. Two distinct fractions are obtained, an aqueous phase and an organic phase. The aqueous fraction is distilled by the equipment assembly (5) through the thin film evaporator and consists of recoverable products, such as levulinic acid, mono-, di- and trisaccharide sugars, furfural, 5-hydroxymethyl furfural and lactic acid.

The organic phase is concentrated by distillation, in the distillation equipment assembly (5) under reduced pressure.

For the characterization of this product, DPPH (2,2-diphenyl-1-picrylhydrazyl) was chosen, the latter being the most common, among the various existing methods to evaluate the antioxidant activity. This assay is referred to as IC50, i.e. the concentration required to reduce 50% of the DPPH radical, wherein the lower the IC50 value, the greater the antioxidant activity of the material. Therefore, in this case the value obtained for the product was within the range of 20 to 30 mg/ml.

Example 8

Continuous addition, through the assembly (1), of 100 kg/hr of algae, on 80% wet basis, to the reactor (2) containing 200 kg of 2-ethyl-hexanol and DEG and 6 kg of p-toluenesulfonic acid. From this value is withdrawn the same mass value as that which was added of algae, on dry basis, per kg of product, containing a complex mixture of phenolic compounds, glycosides, levulinic acid, mono-, di- and trisaccharide sugars, furfural and 5-hydroxymethyl furfural, to be extracted in the next step. Algae will be continuously added to the reactor (2) at a rate of 100 kg/hr and the same mass value of algae, on dry basis, per hour of liquefied, is withdrawn. The temperature inside the reactor (2) is within the range of 120° C. to 180° C.

The product obtained by this catalytic thermochemical process is subjected to a liquid-liquid extraction in the separation equipment (4) in the presence of distilled water. The extraction is carried out in an amount of 50% of the product mass per 50% of distilled water. Two distinct fractions are obtained, an aqueous phase and an organic phase. The aqueous fraction is distilled by the equipment assembly (5) through the thin film evaporator and consists of recoverable products, such as levulinic acid, mono-, di- and trisaccharide sugars, furfural, 5-hydroxymethyl furfural and lactic acid.

The organic phase is concentrated by distillation, in the distillation equipment assembly (5) under reduced pressure.

For the characterization of this product, DPPH (2,2-diphenyl-1-picrylhydrazyl) was chosen, the latter being the most common, among the various existing methods to evaluate the antioxidant activity. This assay is referred to as IC50, i.e. the concentration required to reduce 50% of the DPPH radical, wherein the lower the IC50 value, the greater the antioxidant activity of the material. Therefore, in this case the value obtained for the product was within the range of 15 to 20 mg/ml.

Example 9

Continuous addition, through the assembly (1), of 300 kg/hr of sludge from waste water treatment plants, on 80% wet basis, to the reactor (2) containing 200 kg of 2-ethyl-hexanol and DEG and 6 kg of p-toluenesulfonic acid. From this value is withdrawn the same mass value as that which was added of sludge from waste water treatment plants, on dry basis, per kg of product, containing a complex mixture of phenolic compounds, glycosides, to be extracted in the next step. Sludge from water treatment plants will be continuously added to the reactor (2) at a rate of 300 kg/hr and the same mass value of sludge from waste water treatment plants, on dry basis, per hour of liquefied, is withdrawn. The temperature inside the reactor (2) is within the range of 120° C. to 180° C.

The product obtained by this catalytic thermochemical process is subjected to a liquid-liquid extraction in the separation equipment (4) in the presence of condensed water obtained. The extraction is carried out in an amount of 50% of the product mass per 50% of condensed water. Two distinct fractions are obtained, an aqueous phase and an organic phase.

The organic phase is concentrated by distillation, in the distillation equipment assembly (5) under reduced pressure.

For the characterization of this product, DPPH (2,2-diphenyl-1-picrylhydrazyl) was chosen, the latter being the most common, among the various existing methods to evaluate the antioxidant activity. This assay is referred to as IC50, i.e. the concentration required to reduce 50% of the DPPH radical, wherein the lower the IC50 value, the greater the antioxidant activity of the material. Therefore, in this case the value obtained for the product was within the range of 20 to 30 mg/ml.

Example 10

Continuous addition, through the assembly (1), of 100 kg/hr of beer dreche, as for instance its sludge, on 60% wet basis, to the reactor (2) containing 400 kg of 2-ethyl-hexanol and DEG and 12 kg of p-toluenesulfonic acid. From this value is withdrawn the same mass value as that which was added on dry basis, per kg of product, containing a complex mixture of phenolic compounds, glycosides, levulinic acid, mono-, di- and trisaccharide sugars, furfural and 5-hydroxymethyl furfural to be extracted in the next step. Beer dreche will be continuously added to the reactor (2) at a rate of 100 kg/hr and the same mass value of beer dreche, on dry basis, per hour of liquefied, is withdrawn. The temperature inside the reactor (2) is within the range of 120° C. to 180° C.

The product obtained by this catalytic thermochemical process is subjected to a liquid-liquid extraction in the separation equipment (4) in the presence of condensed water obtained. The extraction is carried out in an amount of 90% of the product mass per 10% of condensed water. Two distinct fractions are obtained, an aqueous phase and an organic phase. The aqueous fraction is distilled by the equipment assembly (5) through the thin film evaporator and consists of recoverable products, such as levulinic acid, mono-, di- and trisaccharide sugars, furfural, 5-hydroxymethyl furfural and lactic acid.

The organic phase is concentrated by distillation, in the distillation equipment assembly (5) under reduced pressure. For the characterization of this product, DPPH (2,2-diphenyl-1-picrylhydrazyl) was chosen, the latter being the most common, among the various existing methods to evaluate the antioxidant activity. This assay is referred to as IC50, i.e. the concentration required to reduce 50% of the DPPH radical, wherein the lower the IC50 value, the greater the antioxidant activity of the material. Therefore, in this case the value obtained for the product was within the range of 20 to 30 mg/ml.

Example 11

Continuous addition, through the assembly (1), of 100 kg/hr of algae, on 80% wet basis, to the reactor (2) containing 200 kg of glycerine and 7 kg of p-toluenesulfonic acid. From this value is withdrawn the same mass value as that which was added on dry basis, per kg of product, containing a complex mixture of phenolic compounds, glycosides, levulinic acid, mono-, di- and trisaccharide sugars, furfural and 5-hydroxymethyl furfural to be extracted in the next step. Algae will be continuously added to the reactor (2) at a rate of 100 kg/hr and the same mass value of algae, on dry basis, per hour of liquefied, is withdrawn. The temperature inside the reactor (2) is within the range of 120° C. to 180° C.

The product obtained by this catalytic thermochemical process is subjected to a liquid-liquid extraction in the separation equipment (4) in the presence of distilled water. The extraction is carried out in an amount of 50% of the product mass per 50% of distilled water. Two distinct fractions are obtained, an aqueous phase and an organic phase. The aqueous fraction is distilled by the equipment assembly (5) through the thin film evaporator and consists of recoverable products, such as levulinic acid, mono-, di- and trisaccharide sugars, furfural, 5-hydroxymethyl furfural and lactic acid.

The organic phase is concentrated by distillation, in the distillation equipment assembly (5) under reduced pressure.

For the characterization of this product, DPPH (2,2-diphenyl-1-picrylhydrazyl) was chosen, the latter being the most common, among the various existing methods to evaluate the antioxidant activity. This assay is referred to as IC50, i.e. the concentration required to reduce 50% of the DPPH radical, wherein the lower the IC50 value, the greater the antioxidant activity of the material. Therefore, in this case the value obtained for the product was within the range of 15 to 20 mg/ml.

Example 12

Continuous addition, through the assembly (1), of 300 kg/hr of waste from the paper industry, as for instance its sludge, on 70% wet basis, to the reactor (2) containing 300 kg of 1-octanol and 12 kg of p-toluenesulfonic acid. From this value is withdrawn the same mass value as that which was added of waste from the paper industry, on dry basis, per kg of product, containing a complex mixture of phenolic compounds, glycosides, levulinic acid, mono-, di- and trisaccharide sugars, furfural and 5-hydroxymethyl furfural, to be extracted in the next step. Waste from paper industry will be continuously added to the reactor (2) at a rate of 300 kg/hr and the same mass value of waste from paper industry, on dry basis, per hour of liquefied, is withdrawn. The temperature inside the reactor (2) is within the range of 120° C. to 180° C.

The product obtained by this catalytic thermochemical process is subjected to a liquid-liquid extraction in the separation equipment (4) in the presence of condensed water obtained. The extraction is carried out in an amount of 50% of the product mass per 50% of condensed water. Two distinct fractions are obtained, an aqueous phase and an organic phase. The aqueous fraction is distilled by the equipment assembly (5) through the thin film evaporator and consists of recoverable products, such as levulinic acid, mono-, di- and trisaccharide sugars, furfural, 5-hydroxymethyl furfural and lactic acid.

The organic phase is concentrated by distillation, in the equipment assembly (5) under reduced pressure.

For the characterization of this product, DPPH (2,2-diphenyl-1-picrylhydrazyl) was chosen, the latter being the most common, among the various existing methods to evaluate the antioxidant activity. This assay is referred to as IC50, i.e. the concentration required to reduce 50% of the DPPH radical, wherein the lower the IC50 value, the greater the antioxidant activity of the material. Therefore, in this case the value obtained for the product was within the range of 20 to 30 mg/ml.

Example 13

Continuous addition, through the assembly (1), of 100 kg/hr of pellets of fuel derived from waste, on 20% wet basis, to the reactor (2) containing 800 kg of industrial waste from the regeneration and recycling of used vegetable and mineral oils and 2-ethyl-hexanol and 35 kg of p-toluenesulfonic acid. From this value is withdrawn the same mass value as that which was added of fuel derived from waste, on dry basis, per kg of product, containing a complex mixture of phenolic compounds, glycosides, levulinic acid, mono-, di- and trisaccharide sugars, furfural and 5-hydroxymethyl furfural, to be extracted in the next step. Pellets of fuel derived from waste will be continuously added to the reactor (2) at a rate of 100 kg/hr and the same mass value, on dry basis, per hour of liquefied, is withdrawn. The temperature inside the reactor (2) is within the range of 120° C. to 180° C.

The product obtained by this catalytic thermochemical process is subjected to a liquid-liquid extraction in the separation equipment (4) in the presence of 50%/50% water and ethanol solution. The extraction is carried out in an amount of 30% of product mass per 70% of water and ethanol solution. Two distinct fractions are obtained, an aqueous phase and an organic phase. The aqueous fraction is distilled by the equipment assembly (5) through the thin film evaporator and consists of recoverable products, such as levulinic acid, mono-, di- and trisaccharide sugars, furfural, 5-hydroxymethyl furfural and lactic acid.

The organic phase is concentrated by distillation, in the distillation equipment assembly (5) under reduced pressure.

For the characterization of this product, DPPH (2,2-diphenyl-1-picrylhydrazyl) was chosen, the latter being the most common, among the various existing methods to evaluate the antioxidant activity. This assay is referred to as IC50, i.e. the concentration required to reduce 50% of the DPPH radical, wherein the lower the IC50 value, the greater the antioxidant activity of the material. Therefore, in this case the value obtained for the product was within the range of 20 to 30 mg/ml.

Example 14

Continuous addition, through the assembly (1), of 500 kg/hr of forest residues, such as eucalyptus sawdust, on 40% wet basis, in the reactor (2) containing 600 kg of a mixture of DEG and 2-ethyl-hexanol and 30 kg of p-toluenesulfonic acid. From this value is withdrawn the same mass value as that which was added of forest residues on a dry basis, kg of product, containing a complex mixture of phenolic compounds, glycosides, levulinic acid, mono-, di- and trisaccharide sugars, furfural and 5-hydroxymethyl furfural, to be extracted in the next step. Forest residues, such as eucalyptus sawdust, will be continuously added to the reactor (2) at a rate of 500 kg/hr and the same mass value of forest residues (eucalyptus sawdust), on a dry basis, per hour of liquefied, is withdrawn. The temperature within the reactor (2) is in the range of 120° C. to 180° C.

The product obtained by this catalytic thermochemical process is subjected to a liquid-liquid extraction in the separation equipment (4) in the presence of condensed water obtained. The extraction is carried out in an amount of 25% of the product mass per 75% of condensed water. Two distinct fractions are obtained, an aqueous phase and an organic phase. The aqueous fraction is distilled by the equipment assembly (5) through the thin film evaporator and consists of recoverable products, such as levulinic acid, mono-, di- and trisaccharide sugars, furfural, 5-hydroxymethyl furfural and lactic acid.

The organic phase is concentrated by distillation, in the equipment assembly (5) under reduced pressure.

For the characterization of this product, DPPH (2,2-diphenyl-1-picrylhydrazyl) was chosen, the latter being the most common, among the various existing methods to evaluate the antioxidant activity. This assay is referred to as IC50, i.e. the concentration required to reduce 50% of the DPPH radical, wherein the lower the IC50 value, the greater the antioxidant activity of the material. Therefore, in this case the value obtained for the product was within the range of 12 to 15 mg/ml.

As will be evident to the person skilled in the art, this invention should not be limited to the embodiments described herein, and a number of changes are possible which remain within the scope of the present invention.

Obviously, the preferred embodiments described above are combinable, in the different possible forms, the repetition of all such combinations being herein avoided.

Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skilled in the art that a contradiction or inconsistency would arise.

The disclosure should not be seen in any way restricted to the embodiments described and a person with ordinary skill in the art will foresee many possibilities to modifications thereof.

The following claims further set out particular embodiments of the disclosure.

The invention claimed is:

1. A process for the production of compounds derived from organic materials and/or waste, comprising:

a) continuous depolymerization and solvolysis of organic materials and/or waste that are continuously added, thereby obtaining a product;

b) liquid-liquid extraction of sugars, polysaccharides and phenolic compounds of the product obtained in step (a) by adding an amount of from 10 to 75 wt. % water, ethanol or a mixture of water and ethanol, thereby obtaining an organic phase and an aqueous phase;

c) distillation of the organic phase obtained in step (b); and d) evaporation of volatile compounds from the aqueous phase obtained in step (b).

2. The process according to claim 1, wherein said organic materials and/or waste are added at a rate of 10 to 50 wt. % per hour relative to the mass of a solvent or mixture of solvents, wherein the solvent or mixture of solvents is selected from the group consisting of DEG-type glycols (diethyleneglycol) and glycerine, alcohols selected from 1-octanol, or 2-octanol or 2-ethyl-hexanol, mineral or vegetable oils and industrial waste from the recycling and regeneration of used mineral and vegetable oils, and wherein the process is carried out in the presence of an organic or mineral acid catalyst.

3. The process according to claim 1, wherein the boiling point of the organic phase obtained in step (b) ranges from 100 to 240° C.

4. The process according to claim 1, wherein the ratio of the product obtained in step (a) relative to the amount of organic materials and/or waste added is between 70 and 99 wt. %.

5. The process according to claim 4, wherein said organic materials and/or waste are selected from the group consisting of: forest residues, vegetable residues, sludge from urban water treatment plants, livestock industry, sludge from paper industry, beer dreche, algae, residues from the potato or tomato industry, pellets and pellet industry waste, fuel derived from waste and pellets of fuel derived from waste.

6. The process according to claim 2, wherein said glycol is is-diethylene glycol (DEG); and wherein said alcohols are selected from the group consisting of 1-octanol, 2-octanol, 2-ethylhexanol.

7. The process according to claim 2, wherein said solvent or mixture of solvents is distilled from the reaction mixture together with the water present in the organic materials and/or waste inserted in a range of 5 to 60% of mass concentration.

8. The process according to claim 1, wherein said organic materials and/or waste comprise water between 0.1 and 90% (w/w).

9. The process according to claim 1, wherein said organic materials and/or waste have in their composition a water content between 30 and 60% (w/w).

10. The process according to claim 1, wherein said aqueous phase of step (b) comprises recoverable compounds, said compounds being selected from the group consisting of: levulinic acid, mono-, di- and trisaccharide sugars, furfural, 5-hydroxymethyl furfural and lactic acid, at a concentration of between 3 and 99% (dry w/w).

11. The process according to claim 1, wherein said organic phase of step (b) comprises an alcohol content between 1 and 50% and phenolic compounds (w/w).

12. The process according to claim 1, characterized in that the rate of product production is in the range of 5 to 100% (w/w) relative to the added organic materials and/or waste.

13. The process according to claim 2, wherein said organic acid catalyst is added in an amount of from 0.5 to 5% by mass relative to the mass of a solvent or mixture of solvents, and is selected from the group consisting of p-toluenesulfonic acid and sulfuric acid.

14. The process according to claim 2, wherein said mineral acid catalyst is added in an amount of from 0.5 to 5% ($w_{mineral\ acid\ catalyst}/w_{total\ weight\ of\ reaction\ mixture}$) relative to the total weight of a reaction mixture, and is selected from the group consisting of aluminium sulphate and aluminium chloride.

15. The process according to claim 1, wherein step (a) is carried out at a temperature of from 120° C. to 180° C.

* * * * *